United States Patent
Zoicas

(10) Patent No.: US 10,856,797 B2
(45) Date of Patent: Dec. 8, 2020

(54) METHOD AND SYSTEM FOR MONITORING THE AUTONOMIC NERVOUS SYSTEM OF A SUBJECT

(71) Applicant: SOCIETE CODESNA, Nice (FR)

(72) Inventor: Vasile Zoicas, La Gaude (FR)

(73) Assignee: SOCIETE CODESNA, Nice (FR)

( * ) Notice: Subject to any disclaimer, the term of this patent is extended or adjusted under 35 U.S.C. 154(b) by 964 days.

(21) Appl. No.: 15/119,276

(22) PCT Filed: Feb. 17, 2015

(86) PCT No.: PCT/EP2015/053345
§ 371 (c)(1),
(2) Date: Jan. 18, 2017

(87) PCT Pub. No.: WO2015/121503
PCT Pub. Date: Aug. 20, 2015

(65) Prior Publication Data
US 2017/0127994 A1   May 11, 2017

(30) Foreign Application Priority Data

Feb. 17, 2014   (FR) ..................................... 14 51257

(51) Int. Cl.
*A61B 5/024*       (2006.01)
*A61B 5/00*        (2006.01)
(Continued)

(52) U.S. Cl.
CPC .......... *A61B 5/4035* (2013.01); *A61B 5/0245* (2013.01); *A61B 5/02405* (2013.01);
(Continued)

(58) Field of Classification Search
None
See application file for complete search history.

(56) References Cited

U.S. PATENT DOCUMENTS

2007/0299354 A1   12/2007   Striepe et al.
2012/0136226 A1    5/2012   Wilke

OTHER PUBLICATIONS

International Search Report for corresponding International PCT application No. PCT/EP2015/053345, dated Jun. 2, 2015.
(Continued)

*Primary Examiner* — Carl H Layno
*Assistant Examiner* — Jon Eric C Morales
(74) *Attorney, Agent, or Firm* — Hauptman Ham, LLP

(57) ABSTRACT

Method and system for monitoring the autonomic nervous system (ANS) of a subject, comprising acquiring at least one physiological signal having W heartbeats, generating data which is a function of the variability of the heart rate on the W heartbeats, with the HRV having W−1 RR intervals separating two consecutive heartbeats detected respectively at the moments tk−1 and tk, each RR interval having a duration of value $a_K = t_K - t_K - 1$ with $k = (X-W+2) \ldots X$; calculating at least one parameter taken from the parameter TAS(tx) representing the level of activity of the sympathetic system and/or the parameter TAP(tx) representing the level of activity of the parasympathetic system; and/or other parameters such as the parameter SL(tx) representing stress level of the subject at the moment tx and calculated using the equation such that $SL(tx) = 100 + TAS(tx) - TAP(tx)$; and supplying data representative of at least one parameter.

21 Claims, 5 Drawing Sheets

(51) Int. Cl.
*A61B 5/0245* (2006.01)
*A61B 5/0456* (2006.01)
*A61B 5/16* (2006.01)
*A63F 13/212* (2014.01)

(52) U.S. Cl.
CPC ........ *A61B 5/02416* (2013.01); *A61B 5/0456* (2013.01); *A61B 5/165* (2013.01); *A61B 5/681* (2013.01); *A61B 5/744* (2013.01); *A61B 5/7415* (2013.01); *A61B 5/486* (2013.01); *A63F 13/212* (2014.09)

(56) References Cited

OTHER PUBLICATIONS

Camillo Cammarota, et al., "Analysis of Stationary Periods of Heart Rate via Symbolic Dynamics," Field Programmable Logic and Application, Jan. 1, 2002, Springer Berlin Heidelberg, Berlin, Heidelberg, vol. 2526, pp. 13-19.
G. Graff, et al., "Ordinal Pattern Statistics for the Assessment of Heart Rate Variability," The European Physical Journal Special Topics, Jun. 1, 2013, pp. 525-534.
A. Porta, et al., "Temporal Asymmetries of Short-term Heart Period Variability are Linked to Autonomic Regulation," American Journal of Physiology Regulatory, Integrative and Comparative Physiology, vol. 295, No. 2, Jun. 11, 2008, pp. R550-R557.

HRV without false beats

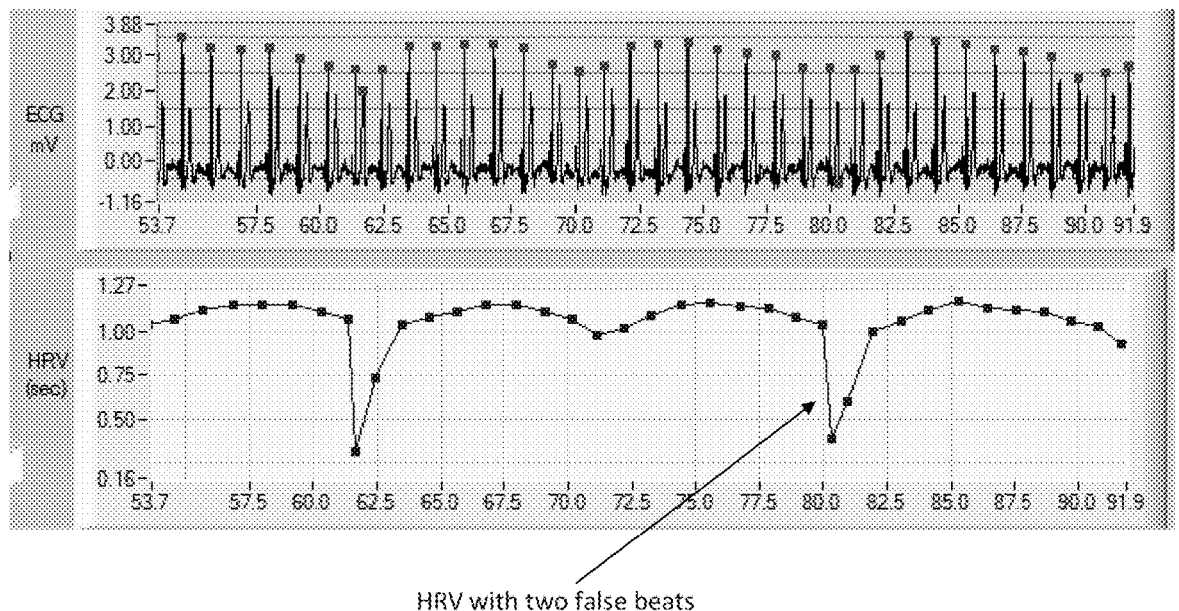
HRV with two false beats
Figure 6(b)
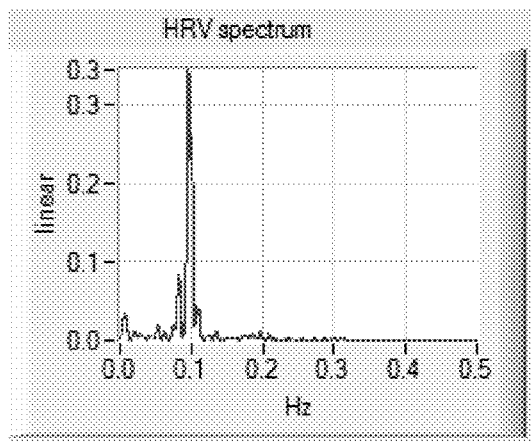 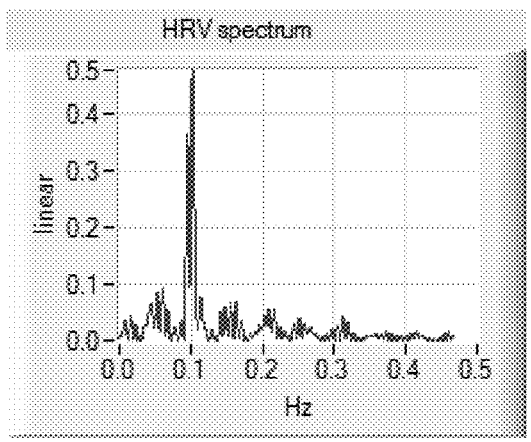
Figure 6(c)          Figure 6(d)

METHOD AND SYSTEM FOR MONITORING THE AUTONOMIC NERVOUS SYSTEM OF A SUBJECT

TECHNICAL FIELD OF THE INVENTION

This invention in general relates to a system for monitoring the autonomic nervous system (ANS). The invention proposes moreover, a method and a system for assisting in the regulating of the activity of the ANS. It has for particular advantage systems for monitoring or for regulating that require a following of the ANS in real time or at the very least with very good reactivity.

PRIOR ART

The autonomic nervous system (ANS) is the part of the nervous system that is responsible for automatic functions that are not subject to voluntary control of a living being such as a person. The ANS is comprised of two branches, respectively the sympathetic system and the parasympathetic system. The roles of the sympathetic and parasympathetic systems are different and they generally exert antagonistic effects on the same target organs. Generally, the sympathetic system assists the body in responding to emergency situations in order to accelerate the reactions of the neurons in order to increase for example the frequency of the heartbeats and to slow down the process of digestion.

On the other hand, the parasympathetic system helps the body to preserve and to restore its energy. When a person relaxes, for example by resting in a chair, the parasympathetic system lowers the blood pressure, slows down the frequency of the heartbeats and accelerates the process of digestion.

Prolonged stress generates negative emotional activity that stimulates the sympathetic system by creating as such a constant imbalance that causes many symptoms. In order to supply researchers and doctors with precise data in order to perform diagnostics and to decide suitable treatments, there is then a need consisting in reliably and accurately monitoring the sympathetic and parasympathetic systems and in giving a representation thereof that is easy to interpret. An interpretation of the ANS can make it possible to identify a particular pathology such as for example a state in which the sympathetic system of a patient is abnormally active with respect to the parasympathetic system. As such, the doctor can perform diagnostics and decide suitable remedies.

There are many methods for monitoring and analyzing the ANS.

The Heart Rate Variability (HRV) is in general used to evaluate physiological functions such as the activities of the sympathetic and parasympathetic systems. The HRV can be generated for example by using the data from a sequence of intervals between beats in a physiological signal such as an electrocardiogram signal (ECG). Most often, an interval/offset between two successive heartbeats, referred to as "RR interval", is defined as an interval of time between two preferentially successive spikes of an R wave of an ECG signal.

There are many analysis and signal treatment methods using the HRV, of which most are based on an analysis in the frequency domain. However, frequency analyses have several disadvantages in particular in terms of precision and execution time.

Indeed, these frequency analyses require implementing mathematical functions such as the Fast Fourier Transformation usually designated by the acronym FFT) or/and the Complex Demodulation Method (CDM), described in documents U.S. Pat. No. 7,079,888 and US20130009779A1. However these mathematical functions require a long time for recording and therefore cannot be carried out in real time.

In addition, it is difficult to correctly separate in the frequency domain the data that belongs respectively to the sympathetic system and to the parasympathetic system. In other words, the two sympathetic and parasympathetic systems cannot be analyzed easily independently.

Frequency analyses are furthermore very sensitive to the noise of an ECG signal such as the false beats generated during the capturing of the signal for example in the case where the person moves about during a sports activity or if the ECG sensor is not operating correctly. Frequency analyses are also sensitive to atypical beats such as extrasystoles, arrhythmias (bigeminy, trigeminy), etc. As such, the data transformed in the frequency domain are highly distorted due to noise or false beats, which considerably reduces the precision of the monitoring of the ANS. Frequency analyses based on known methods are therefore not very reliable when the patient has symptoms that result in atypical beats, or/and in the case where false beats are generated for example by a detector with low performance or operating in unfavorable acquisition conditions.

Other solutions propose analyses carried out in the temporal domain. These known solutions provide for, as is the case in document US20130079652A1, calculations such as a measurement selected from a set of measurements comprising a mean RR interval, a standard deviation of the RR intervals, a ratio of the standard deviations according to various axes of a scatter diagram of the RR intervals, a difference between the ratios of the standard deviations, a standard deviation of a mean of RR intervals in various segments of time, etc.

The temporal analysis calculations as mentioned hereinabove can be carried out in real time. On the other hand, these calculations also do not make it possible to analyze the two sympathetic and parasympathetic systems independently. For example, if the sympathetic system of a patient remains active longer than a predetermined period and prevents the parasympathetic system from playing its role of recovery, this cannot be reflected by the result of these temporal analysis calculations. These calculations do not make it possible to analyze the state of balance between the two sympathetic and parasympathetic systems of the ANS and as such do not make it possible to determine with precision the stress level of a patient.

Consequently, there is a need consisting in proposing a solution that makes it possible to supply a reliable, simple and fast analysis for monitoring the sympathetic and parasympathetic systems independently, with good reactivity and preferably in real time and while limiting the sensitivity to disturbing factors such as atypical beats and noise such as false beats generated during the capturing of ECG signals.

SUMMARY OF THE INVENTION

In order to reach this objective, an aspect of this invention relates to a method for monitoring an autonomic nervous system (ANS) of a subject, comprising the following steps:
acquiring at least one physiological signal comprising W heartbeats, with each heartbeat being detected at a moment t, with t between $t_{X-W+1}$ and $t_X$, the moment $t_X$ being the last beat of the W heartbeats;
generating a data which is a function of the variability of the heart rate (HRV) over all of the W heartbeats, with the HRV comprising W−1 RR intervals separating two consecutive heartbeats detected respectively at the moments $t_{k-1}$ and $t_k$, with each RR interval having a duration with a value $a_k = t_k - t_{k-1}$ with k=(X−W+2) ... X;

using at least one microprocessor to calculate at least one parameter taken from:

the parameter $TAS(t_X)$ representing the level of activity of the sympathetic system and which is according to the ratio between on the one hand a first sum obtained by summing, among the values $a_k$, only those that are greater than the value $a_{k-1}$ of the immediately preceding interval therefore only the values $a_k$ that satisfy the following condition $a_k > a_{k-1}$, $a_{k-1}$ being the duration of the interval immediately preceding that of the value ak and a second sum obtained by summing all of the W−1 values $a_k$; and/or the parameter $TAP(t_X)$ representing the level of activity of the parasympathetic system and which is according to the ratio between on the one hand a first sum obtained by summing, among the values $a_k$, only those that are less than the value $a_{k-1}$ of the immediately preceding interval and a second sum obtained by summing all of the W−1 values $a_k$;

the parameter SL(tX) representing a stress level of the subject (10) at the moment tX and calculated by applying the following equation:

$$SL(t_X) = 100 + TAS(t_X) - TAP(t_X);$$

supplying a data representative of said at least one parameter. In an alternative or complementary manner, the method comprises using at least one microprocessor to calculate at least one parameter taken from:

the parameter $TPSP(t_X)$ representing the rate of pollution from the sympathetic system to the parasympathetic system and which is according to the ratio between on the one hand a first sum obtained by summing, among the values $a_k$, only those that satisfy the following condition: $a_k < a_{k-1}$ and $a_{k-1} > a_{k-2}$ and $a_{k-1} > a_k$ and on the other hand a second sum obtained by summing all of the W−1 values $a_k$; and/or the parameter $TPPS(t_X)$ representing the rate of pollution from the parasympathetic system to the sympathetic system and which is according to the ratio between on the one hand a first sum obtained by summing, among the values $a_k$, only those that satisfy the following condition: ($a_k > a_{k-1}$ and $a_{k-1} < a_{k-2}$ and $a_{k-1} < a_k$) and on the other hand a second sum obtained by summing all of the W−1 values $a_k$;

As such, the method according to the invention makes it possible to temporally analyze the two sympathetic and parasympathetic branches of the ANS system, independently and in real time or at least with improved reactivity. It is as such possible to retroact in real time in order to modify the activity of the ANS according to the purpose sought: for example a reduction in the stress or an increase in the intensity of the emotions.

Moreover, the method according to the invention makes it possible to monitor the sympathetic and parasympathetic systems independently and while limiting the sensitivity to disturbing factors such as atypical beats and noise such as false beats.

In the framework of this invention, the term subject designates any person or animal for which the heartbeat can be detected.

Note that this invention also relates to the cases where only one or some of the parameters TAS, TAP, TPPS, TPSP, TAS(tx), TAP(tx), TPPS(tx), TPSP(tx), $\overline{TPSP}$, $\overline{TPPS}$, SL, RSL, SL($t_X$), RSL($t_X$) is calculated.

The invention also relates to the methods in which one of these parameters and one or several of the other parameters is calculated.

At least the steps of generating and of calculating are implemented by computer, i.e. they are executed by at least one microprocessor.

Optionally, the invention comprises at least one of any of the following characteristics and steps taken individually or in combination:

In the following equations $a_{k-1}$=value of the interval of time immediately preceding the internal of time of duration $a_k$, i.e. $a_{k-1} = t_{k-1} - t_{k-2}$, and k=(X−W+2), (X−W+3) ... X.

the $TAS(t_X)$ representing the level of activity of the sympathetic system and wherein the $TAS(t_X)$ is calculated by applying the following equation:

$$TAS(t_X) = 100 \cdot \frac{\sum_{k=X-W+2}^{X} (t_k - t_{k-1}) \text{ if } (a_k \leq a_{k-1})}{\sum_{k=X-W+2}^{X} (t_k - t_{k-1})}$$

the $TAP(t_X)$ representing the level of activity of the parasympathetic system and wherein the TAP(tX) is calculated by applying the following equation:

$$TAP(t_X) = 100 \cdot \frac{\sum_{k=X-W+2}^{X} (t_k - t_{k-1}) \text{ if } (a_k \geq a_{k-1})}{\sum_{k=X-W+2}^{X} (t_k - t_{k-1})}$$

with the TPSP(tx) calculated by applying the following equation:

$$TPSP(t_X) = 100 \cdot \frac{\sum_{k=X-W+2}^{X} (t_k - t_{k-1}) \text{ if } (a_k < a_{k-1} \text{ and } a_{k-1} > a_{k-2} \text{ and } a_{k+1} > a_k)}{\sum_{k=X-W+2}^{X} (t_k - t_{k-1})}$$

As such, the $TPSP(t_X)$ is calculated in such a way as to obtain a third partial sum by accumulation of the values $a_k$ of which each one disturbs the increasing monotonous trend formed by RR intervals adjacent to the RR interval corresponding to the value $a_k$ and to divide said third partial sum by the sum of all of the W−1 values $a_k$;

the $TPPS(t_X)$ being calculated by applying the following equation:

$$TPPS(t_X) = 100 \cdot \frac{\sum_{k=X-W+2}^{X} (t_k - t_{k-1}) \text{ if } (a_k > a_{k-1} \text{ and } a_{k-1} < a_{k-2} \text{ and } a_{k+1} < a_k)}{\sum_{k=X-W+2}^{X} (t_k - t_{k-1})}$$

As such, the $TPPS(t_x)$ is calculated in such a way as to obtain a third partial sum by accumulation of the values $a_k$ of which each one disturbs the decreasing monotonous trend formed by RR intervals adjacent to the RR interval corresponding to the value $a_k$ and to divide said third partial sum by the sum of all of the W−1 values $a_k$.

In addition, the invention relates to two parameters $\overline{TPSP}$ and $\overline{TPPS}$ as hereinbelow:

the parameter $\overline{TPSP}$ representing the approximate rate of pollution of the sympathetic to the parasympathetic system and calculated by applying the following equation:

$$\overline{TPSP} = 100 \cdot \frac{\sum_{n=1}^{N-1} 1 \text{ if } (a_n < a_{n-1} \text{ and } a_{n-1} > a_{n-2} \text{ and } a_{n+1} > a_n)}{N-1}$$

the parameter $\overline{TPPS}$ representing the approximate rate of pollution from the parasympathetic system to the sympathetic system and calculated by applying the following equation:

$$\overline{TPPS} = 100 \cdot \frac{\sum_{n=1}^{N-1} 1 \text{ if } (a_n > a_{n-1} \text{ and } a_{n-1} < a_{n-2} \text{ and } a_{n+1} < a_n)}{N-1}$$

Preferably, the invention further relates to an application comprising at least the calculation of the parameters $TAS(t_x)$ and $TAP(t_x)$ and comprising the calculation of a parameter $SL(t_x)$ representing a stress level of the subject at the moment $t_x$ and calculated by applying the following equation:

$$SL(t_X) = 100 + TAS(t_X) - TAP(t_X).$$

Preferably, the invention relates to another application comprising the calculation of a parameter $RSL(t_x)$ representing a residual stress level of the subject at the moment tx and calculated by applying the following equation:

$$RSL(t_X) = SL(t_X) \cdot \frac{HR_{Rest}}{HR(t_X)}$$

in which $HR_{Rest}$ is the heart rate at rest, i.e. the subject is inactive for at least 20 seconds and preferably 40 seconds, $HR(t_x)$ is the heart rate at the moment $t_x$.

According to a preferred method, the method comprises:
generating a respiration stimulus supplied to the subject for a duration T, with the respiration stimulus comprising a respiratory setting so that the subject breathes symmetrically;
the duration T being calculated according to at least one data according to the heart rate (HR) of the subject.

According to an embodiment, at least one parameter comprises a value of chronic stress CS which is a function of the parameter $SL(t_x)$ during said duration T.

According to an embodiment, the value of chronic stress CS is equal to the mean value of the parameter $SL(t_x)$ over said duration T of the respiration stimulus.

According to an embodiment, the method comprises the calculating and the displaying of a mathematical correlation between the heart rate (HR) of the subject and a function that controls the respiration stimulus.

According to an embodiment, said data according to the heart rate (HR) is a data representing the heart rate (HR) of the subject.

According to an embodiment, the physiological signal is an electrocardiogram signal (ECG), or any other physiological signal that is a function of the heart rate.

The invention relates to a step of supplying a visual and/or audible representation of said at least one parameter.

Preferably, said at least one parameter is calculated in real time or at regular intervals and comprises a step of supplying a visual representation of the change over time of said at least one parameter. Advantageously, the step of supplying a visual representation comprises the displaying of a graph or of a bar that changes over time.

In another application of the invention, the step of supplying a visual representation of the change over time of said at least one parameter comprises the displaying of at least one avatar and/or of at least one animated object of which the animation or the visual change is a function of the change over time of said at least one parameter.

Preferably, at least two parameters are calculated, with at least one of the parameters being taken from the $TAS(t_x)$ and the $TPSP(t_x)$ and at least one other parameter taken from the $TAP(t_x)$ and the $TPPS(t_x)$ and comprising a step of supplying a visual representation of said at least two parameters, said at least two parameters being represented independently from one another.

Even more advantageously, said at least two parameters are calculated in real time or at regular intervals and comprise a step of supplying a visual representation of the change over time of said at least two parameters.

According to an embodiment, the step of acquiring at least one physiological signal is carried out by at least one of the following devices which are configured to be worn by the subject: an electrocardiogram sensor (ECG), a chest belt, a bracelet or a watch provided with a photoplethysmographic sensor.

According to an embodiment, supplying a data representative of said at least one parameter comprises a displaying on the screen of one from among the following devices: a watch, a telephone, a portable computer, a tablet.

The invention also relates to a computer program product comprising instructions, which when they are carried out by at least one processor, executes the method of monitoring such as hereinabove.

According to an embodiment, the parameters $TAS(t_x)$, $TAP(t_x)$, $TPSP(t_x)$, $TPPS(t_x)$, $SL(t_x)$ and $RSL(t_x)$ can be used in video games and simulators in order to show the current condition of the body of a player such as the stress level, the level of energy, or to simulate a virtual condition of a character in a video game or by a simulator.

In addition, the invention relates to a system for monitoring the autonomic nervous system (ANS) of a subject, comprising a device configured to receive the data of a physiological signal, for example an electrocardiogram signal (ECG), with this physiological signal comprising W heartbeats, with each heartbeat being detected at a moment t, with t between $T_{x-W+1}$ and $t_x$, the moment tx being the last beat of the W heartbeats;

and comprising at least one processing of data provided with at least one processor configured to execute the following steps:

generating of a data which is a function of the variability of the heart rate (HRV) over all of the W heartbeats, with the HRV comprising W−1 RR intervals separating two consecutive heartbeats detected respectively at the moments $t_{k-1}$ and $t_k$, with each RR interval having a duration $a_k=t_k-t_{k-1}$ of a value with $k=(X-W+2)\ldots X$;

calculating at least one parameter taken from:

the parameter TAS $(t_X)$ representing the level of activity of the sympathetic system and which is according to the ratio between on the one hand a first sum obtained by summing, among the values $a_k$, only those that are greater than the value $a_{k-1}$ of the immediately preceding interval therefore only the values $a_k$ that satisfy the following condition $a_k>a_{k-1}$, $a_{k-1}$ being the duration of the interval immediately preceding that of the value $a_k$ and a second sum obtained by summing all of the W−1 values $a_k$; and/or the parameter TAP$(t_X)$ representing the level of activity of the parasympathetic system and which is according to the ratio between on the one hand a first sum obtained by summing, among the values $a_k$, only those that are less than the value $a_{k-1}$ of the immediately preceding interval therefore only the values $a_k$ that satisfy the following condition $a_k<a_{k-1}$, $a_{k-1}$ being the duration of the interval immediately preceding that of the value $a_k$ and a second sum obtained by summing all of the W−1 values $a_k$; and/or the parameter SL(tX) representing a stress level of the subject (10) at the moment tX and calculated by applying the following equation:

$$SL(t_X)=100+TAS(t_X)-TAP(t_X); \text{ and/or}$$

the parameter TPSP(tX) representing the rate of pollution from the sympathetic system to the parasympathetic system and which is according to the ratio between on the one hand a first sum obtained by summing, among the values $a_k$, only those that satisfy the following condition: $a_k<a_{k-1}$ and $a_{k-1}>a_{k-2}$ and $a_{k+1}>a_k$ and on the other hand a second sum obtained by summing all of the W−1 values $a_k$; and/or the parameter TPPS$(t_X)$ representing the rate of pollution from the parasympathetic system to the sympathetic system and which is according to the ratio between on the one hand a first sum obtained by summing, among the values $a_k$, only those that satisfy the following condition: $(a_k>a_{k-1}$ and $a_{k-1}<a_{k-2}$ and $a_{k+1}<a_k)$ and on the other hand a second sum obtained by summing all of the W−1 values $a_k$;

The system comprises a device for displaying, coupled to the data processing module and configured to supply the subject with a data representative of said at least one parameter.

Optionally, the invention comprises at least one of any of the following characteristics taken individually or in combination:

According to an embodiment, the data processing module is configured to carry out the following steps:

generating a respiration stimulus supplied to the subject for a duration T, with the respiration stimulus comprising a respiratory setting so that the subject breathes symmetrically;

the duration T being calculated according to at least one data according to the heart rate (HR) of the subject.

According to an embodiment, at least one parameter that the data processing module is configured to calculate is a value of chronic stress CS, with the value of chronic stress CS being according to the parameter SL(tX) during said duration TL.

According to an embodiment, the value of chronic stress CS is equal to the mean value of the parameter SL(tX) during said duration T of the respiration stimulus.

According to an embodiment, the sensor is one of the following devices which are configured to be worn by the subject: an electrocardiogram sensor (ECG), a chest belt, a photoplethysmographic device installed in a bracelet or in a watch.

According to an embodiment, the data processing module is mechanically integral with the sensor. Alternatively, the data processing module is located at a distance from the sensor and coupled to the sensor by using a wired or wireless communications module.

According to an embodiment, the data processing module is provided on an electronic device such as a mobile telephone, a tablet, a computer, etc.

Preferably, the monitoring system comprises a detector configured to acquire the physiological signal and a device for displaying configured to display a visual representation of said at least one parameter.

Even more advantageously, the monitoring system is configured to provide said subject in real time with a visual representation of said at least one parameter.

The invention relates to a device for assisting in the regulating of the ANS of a subject comprising the monitoring system such as hereinabove.

The invention further relates to a simulator comprising the monitoring system such as hereinabove.

BRIEF DESCRIPTION OF THE FIGURES

The purposes and objects as well as the characteristics and advantages of the invention shall appear better from the detailed description of an embodiment of the latter which is illustrated by the following accompanying drawings wherein:

FIG. 2(*b*) shows the heart rate variability HRV illustrated by N−1 RR intervals $a_1$, $a_2$ to $a_{N-1}$ corresponding respectively to the moments $t_1$, $t_2$ to $t_{N-1}$.

FIG. 6(*b*) shows a portion of a second ECG signal and its HRV, the second ECG signal is obtained by adding two false beats to the first ECG signal.

FIGS. 6(*c*) and 6(*d*) respectively show the spectra of HRV obtained by carrying out a typical frequency analysis of the HRV of the first ECG signal and those for the second ECG signal.

FIG. 7(*b*) shows the results of an example of a calculation of the parameters SL(tx), RSL(tx) and HR(tx) during a rest phase, a phase of sports activity and a recovery phase.

DETAILED DESCRIPTION OF THE INVENTION

Figure 1:
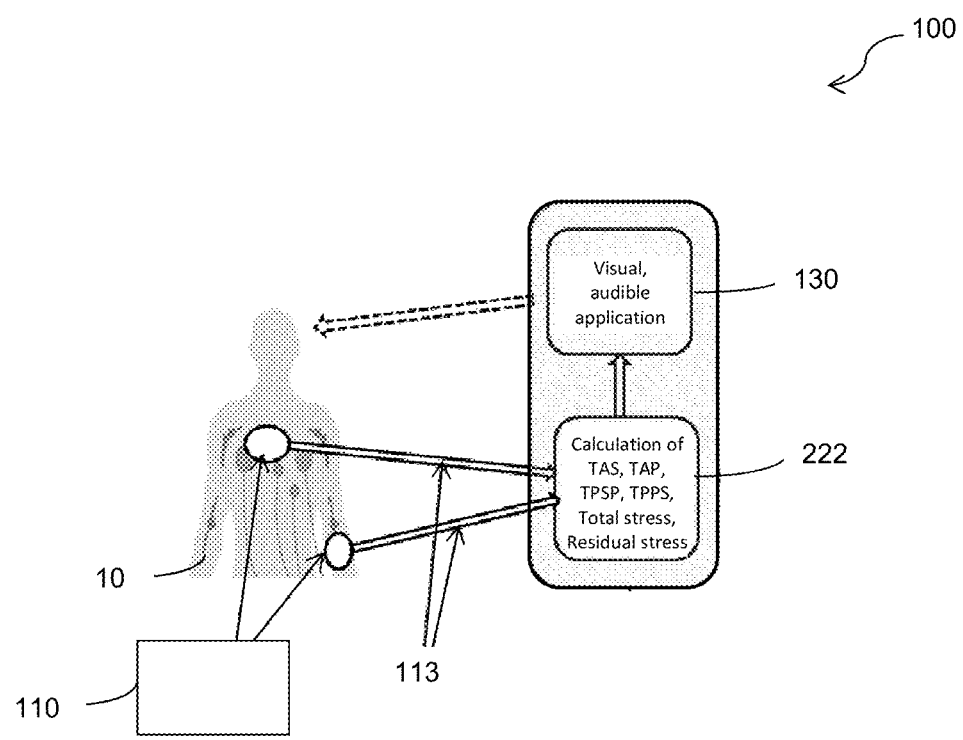
FIG. 1 shows a system for monitoring an autonomic nervous system (ANS) of a living being such as a person according to an example embodiment of the invention.

FIG. 1 shows system for monitoring 100 of the autonomic nervous system (ANS) of a physical subject 10 according to an embodiment of the invention.

The system for monitoring 100, comprises a data processing module 222 and a module for displaying data 130. It is configured to analyze a physiological signal received from a physiological signal sensor 110, typically but not limited to an electrocardiogram (ECG).

The physiological signal sensor 110 is configured to detect heartbeats of the physical person 10 for a certain duration and as such send a physiological signal to the data processing module 222.

Figure 2A:
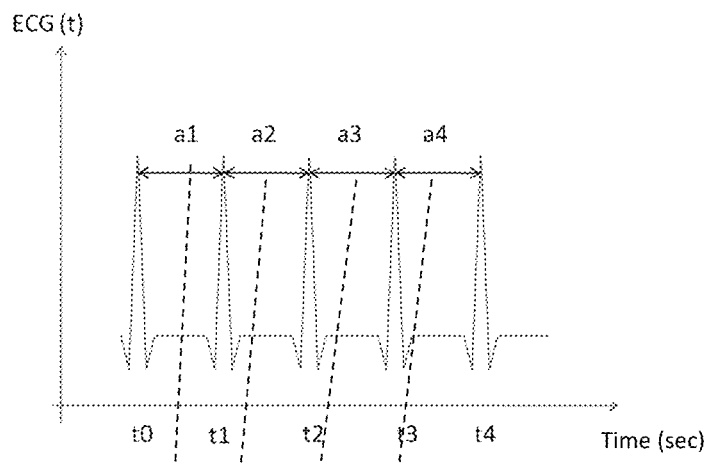
FIG. 2(*a*) show an ECG signal comprising N spikes respectively meaning a heartbeat of the person 10 measured at a moment $t_0$, $t_1$ to $t_{N-1}$ by the ECG sensor 110 according to an embodiment of the invention.

The physiological signal sensor 110 is preferably an electrocardiogram sensor (ECG) configured to generate a physiological signal ECG such as shown in FIG. 2(a) and send this ECG signal to the data processing module 222. This ECG sensor 110 is able to be worn by the person 10 for example on the chest or/and wrist.

In an alternative embodiment, the physiological signal sensor 110 worn by the person 10 can be one of the following devices: a chest belt, a photoplethysmographic device installed in a bracelet or in a watch.

The invention is not limited to methods of acquiring a physiological signal. For example, a signal indicating heartbeats measured by optical devices can also be applied as a source of data for the calculations of the invention.

The data processing module 222 is coupled, by a wired or wireless communication such as by radio waves, to the physiological signal sensor 110. The data processing module 222 is configured to execute a method of analyzing preferably in the temporal domain using a physiological signal such as an ECG signal received from the ECG sensor 110. The data processing module 222 can be carried out either in a device worn by the person 10 or in a device at a distance from the person 10.

According to an embodiment, the data processing module 222 is integral with the physiological signal sensor 110 worn by the person 10. The data processing module 222 and the physiological signal sensor 110 can as such be integrated into a watch or a bracelet for example.

According to another embodiment, the data processing module 222 is a device able to be worn by the person 10, which is mechanically separate from the physiological signal sensor 110. The data processing module 222 and the sensor 110 are separate, while still being coupled in terms of communication.

According to an alternative embodiment, the data processing module 222 is installed in an electronic device such as a mobile telephone, a tablet, a computer, etc.

According to another alternative embodiment, the data processing module 222 is installed in a data server provided with a means for calculating and for processing data.

According to a preferred embodiment, the data processing module 222 itself or the electronic device or the data server hereinabove is provided with a receiver configured to receive the physiological signal sent by the ECG sensor 110.

In the embodiment wherein the data processing module 222 is incorporated into the data server, the physiological signal can be transmitted directly from the ECG sensor 110 to the data server, or via a relay such as an electronic device, for example a mobile telephone, a tablet, a computer, to the data server.

Advantageously, the data processing module 222 is carried out in the form of a piece of software.

In this embodiment, a wired communications module 113 is used to carry out the communication between the ECG sensor 110 and the data processing module 222.

The invention is not limited to means of communication used to carry out the wired or wireless communication between the data processing module 222 and the ECG sensor 110.

Said method of analysis carried out by the data processing module 222 comprises a calculation of RR intervals and of calculations of the parameters TAS, TAP, TPSP, TPPS which shall be described later.

FIG. 2(a) shows an ECG signal comprising N spikes respectively meaning a heartbeat of the person 10 measured at a moment $t_0$, $t_1$ to $t_{N-1}$ by the sensor 110.

Figure 2B:
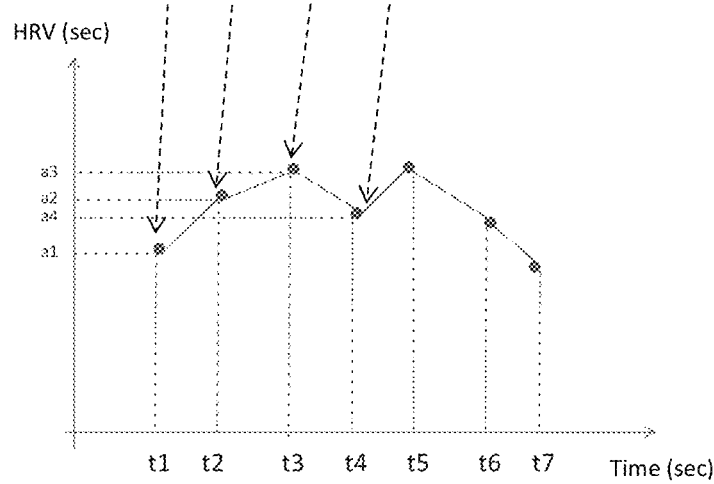

FIG. 2(b) shows a variability of the heart rate HRV illustrated by N−1 RR intervals $a_1$, $a_2$ to $a_{N-1}$ corresponding respectively to the moments $t_1$, $t_2$ to $t_{N-1}$.

Each value $a_n$ of an RR interval is the duration (typically in seconds) that elapses between two adjacent spikes of the ECG signal, with these two spikes corresponding to the two successive heartbeats measured at moments $t_{n-1}$ and $t_n$. The value $a_n$ is represented in the equation (1) hereinbelow:

$$a_n = t_n - t_{n-1} \qquad \text{Eq. (1)}$$

For example, as indicated in FIG. 2(a), the value $a_k$ corresponds to the interval of time RR between the two heartbeats detected at the two moments $t_0$ and $t_1$.

The value of the first interval is noted as $a_1$ and the number n of the RR intervals is equal to N−1.

The data processing module 222 carries out, using the N−1 RR intervals $a_1$, $a_2$ to $a_{N-1}$ of the HRV, calculations of the parameters TAS and TAP having respectively the activity of the sympathetic system and that of the parasympathetic system of the person 10 monitored during a sampling duration TE comprising N heartbeats of the ECG signal.

The calculations of the parameters TAS and TAP use a physiological phenomenon: a duration of an RR interval that decreases between two successive heartbeats indicates a heart rate accelerated by the sympathetic system while a duration of an RR interval that increases between two successive beats indicates a hear rate that is slowed down by the parasympathetic system.

The parameter TAS is configured to represent the rate of sympathetic activity:

$$TAS = 100 \cdot \frac{\sum_{n=1}^{N-1} (t_n - t_{n-1}) \text{ if } (a_n \le a_{n-1})}{\sum_{n=1}^{N-1} (t_n - t_{n-1})} = 100 \cdot \frac{\sum_{n=1}^{N-1} a_n \text{ if } (a_n \le a_{n-1})}{\sum_{n=1}^{N-1} a_n} \qquad \text{Eq. (2)}$$

The parameter TAS is calculated, using the N−1 RR intervals derived from the ECG signal comprising N heartbeats. In order to obtain this parameter, the values an are accumulated (i.e. are summed) if a segment between two values $a_n$ and $a_{n-1}$ is decreasing such as shown in FIG. 2(b); i.e. the values $a_n$ are accumulated of which each one is less than the immediately preceding value $a_{n-1}$. The sum of the values $a_n$ corresponding to the decreasing segments is then divided by the sum of all of the values $a_1$, $a_2$ to $a_{N-1}$.

The parameter TAP is configured to represent the rate of parasympathetic activity:

$$TAP = 100 \cdot \frac{\sum_{n=1}^{N-1} (t_n - t_{n-1}) \text{ if } (a_n \geq a_{n-1})}{\sum_{n=1}^{N-1} (t_n - t_{n-1})} = 100 \cdot \frac{\sum_{n=1}^{N-1} a_n \text{ if } (a_n \geq a_{n-1})}{\sum_{n=1}^{N-1} a_n} \quad \text{Eq. (3)}$$

The parameter TAP is calculated, using the N−1 RR intervals of the HRV derived from the ECG signal comprising N heartbeats, in such a way as to accumulate values $a_n$ if a segment between two values $a_n$ and $a_{n-1}$ is rising such as shown in FIG. 2(b); i.e. values $a_n$ are accumulated of which each one is greater than the immediately preceding value $a_{n-1}$. The sum of the values $a_n$ corresponding to the rising segments is then divided by the sum of all of the values $a_1$, $a_2$ to $a_{N-1}$.

Figure 3:
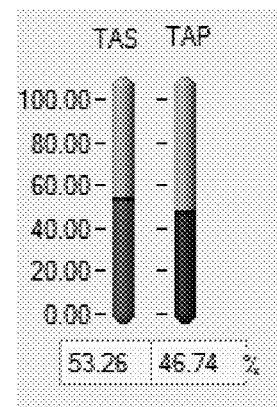
FIG. 3 shows the results of the calculations of two parameters TAS and TAP over a sampling duration TE of 100 heartbeats (N=100).

FIG. 3 shows results of the calculations of the parameters TAS and TAP over a sampling duration TE of 100 heartbeats (N=100). The visual representation of FIG. 3, has for advantage to be able to very easily compare the respective activities of the sympathetic and parasympathetic systems. In this example, the calculation of the parameters TAS and TAP makes it possible to very easily identify that the ANS system of the person 10 is in a relative and imperfect balance because the sympathetic system is slightly more active than that of the parasympathetic system. Moreover, this representation varies in real time in order to follow in real time the change in the respective activities of the sympathetic and parasympathetic systems. This following in real time makes it possible for example for the patient to control his ANS by carrying out appropriate actions, in particular in order to increase the activity of his parasympathetic system.

In terms of the reliability of the calculation from a mathematical standpoint, i.e. in an ideal condition where the ECG signal is correctly captured by the ECG sensor 110, the calculations of the parameters TAS and TAP are, in relation to those of the known methods of frequency analysis, much more precise. The number N of beats can be reduced to a number between 20 and 40.

Comparisons of the two types of calculations (method of the invention and known methods of frequency analysis) shall be supplied in FIGS. 5(a), 5(b) and 6(a) to 6(d) illustrated later.

However, for example when the ECG signal of the person 10 is captured during a sports activity, the number N of beats is more preferably between 200 and 350 (i.e. the duration of the recording of the beats of an ECG signal is about three minutes), because in practice, 200 to 350 successive beats make it possible to reflect a pertinent physiological state.

Indeed, the calculations proposed by the invention make use of simple mathematical implementations, which makes it possible to obtain in real time a calculation result, in particular in an embodiment wherein the number N of heartbeats is less than, for example, 1000.

As such, two parameters TAS(tx) and TAP(tx) respectively showing the activity of the sympathetic system and that of the parasympathetic system, can be calculated, in real time, by using for example a certain number of the last heartbeats measured by the ECG sensor 110.

In a preferred but not limiting embodiment, a sliding sampling window can be used to sample W heartbeats that will be used to calculate the parameters TAS ($t_X$) and TAP($t_X$) of an ECG signal. The invention is not however limited to methods for selecting or for sampling heartbeats used for the calculations of the parameters TAS($t_X$) and TAP($t_X$).

With a sliding window of which the number of samples is W, the data processing module 222 can carry out, at each moment such as a new heartbeat measured at the moment $t_X$ of the ECG signal, calculations of the parameters TAS($t_X$) and TAP($t_X$) in order to obtain in real time results of calculations that show the activity of the sympathetic system and that of the parasympathetic system between two heartbeats (i.e. the $(X-W+1)^{th}$ and the $x^{th}$ heartbeats) respectively at the moments $t_{X-W+1}$ and $t_X$ of the ECG signal.

The number of RR intervals between the two heartbeats at moments $t_{X-W+1}$ and $t_X$ is therefore W−1.

In a preferred but not limiting embodiment, the calculations of the parameters TAS($t_X$) and TAP($t_X$) are carried out after the $W^{th}$ heartbeat of the ECG signal. For example, in order to obtain a result that reflects the activities of the sympathetic and parasympathetic systems, the number of samples W is for example between 10 and 30.

The calculation of the parameter TAS($t_X$) is represented in the equation (4) hereinbelow:

$$TAP(t_X) = 100 \cdot \frac{\sum_{k=X-W+2}^{X} (t_k - t_{k-1}) \text{ if } (a_k \leq a_{k-1})}{\sum_{k=X-W+2}^{X} (t_k - t_{k-1})}, \quad \text{Eq. (4)}$$

in which $a_k = t_k - t_{k-1}$

In a manner close to that of the calculation of the parameter TAS, the parameter TAS($t_X$) is calculated, using the W−1 RR intervals of the HRV derived from a sampling duration TE from the ECG signal comprising W heartbeats between the two heartbeats respectively measured at moments $t_{X-W+1}$ and $t_X$ of the ECG signal, in such a way as to sum the values $a_k$ if a segment between two values $a_k$ and $a_{k-1}$ is decreasing; i.e. the values $a_k$ are accumulated of which each one is less than the immediately preceding value $a_{k-1}$. The sum of the values $a_n$ corresponding to the decreasing segments is then divided by the sum of all of the W−1 values $a_{X-W+2}$, $a_{X-W+3}$ to $a_X$.

The calculation of the parameter TAP($t_X$) follows the equation (5) hereinbelow:

$$TAP(t_X) = 100 \cdot \frac{\sum_{k=X-W+2}^{X}(t_k - t_{k-1}) \text{ if } (a_k \geq a_{k-1})}{\sum_{k=X-W+2}^{X}(t_k - t_{k-1})} \qquad \text{Eq. (5)}$$

In a manner close to that of the calculation of the parameter TAP, the parameter TAP($t_k$) is calculated, using the W−1 RR intervals of the HRV derived from a sampling duration TE comprising W heartbeats between the two heartbeats respectively measured at moments $t_{X-W+1}$ and $t_X$ of the ECG signal, in such a way as to accumulate values $a_k$ if a segment between two values $a_k$ and $a_{k-1}$ is rising; i.e. values $a_k$ are accumulated of which each one is greater than the immediately preceding value $a_{k-1}$. The sum of the values $a_n$ corresponding to the rising segments is then divided by the sum of all of the W−1 values $a_{X-W+2}$, $a_{X-W+3}$ to $a_X$.

Figure 4:
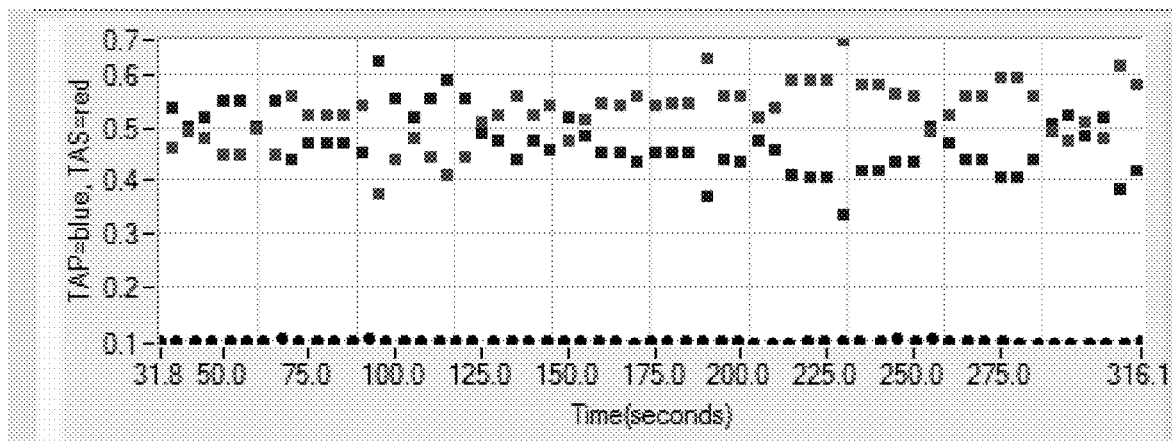
FIG. 4 shows the parameters TAS$(t_X)$ and TAP$(t_X)$ obtained in real time via a calculation based on 30 samples of the sliding window at each moment $t_X$ (W=30).
Figure 5A:
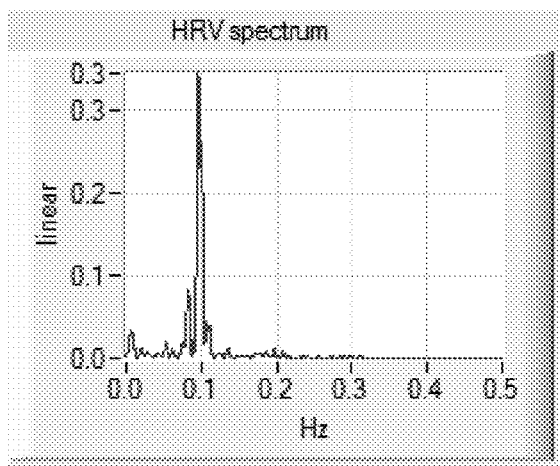
FIGS. 5(*a*) and 5(*b*) each show a spectrum of the HRV according to two types of respiration.
Figure 5B:
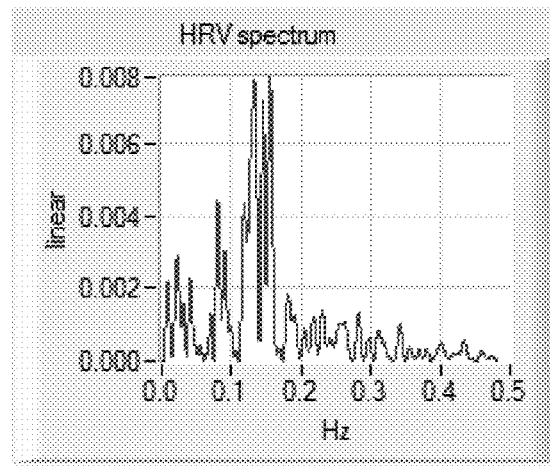
Figure 6A:
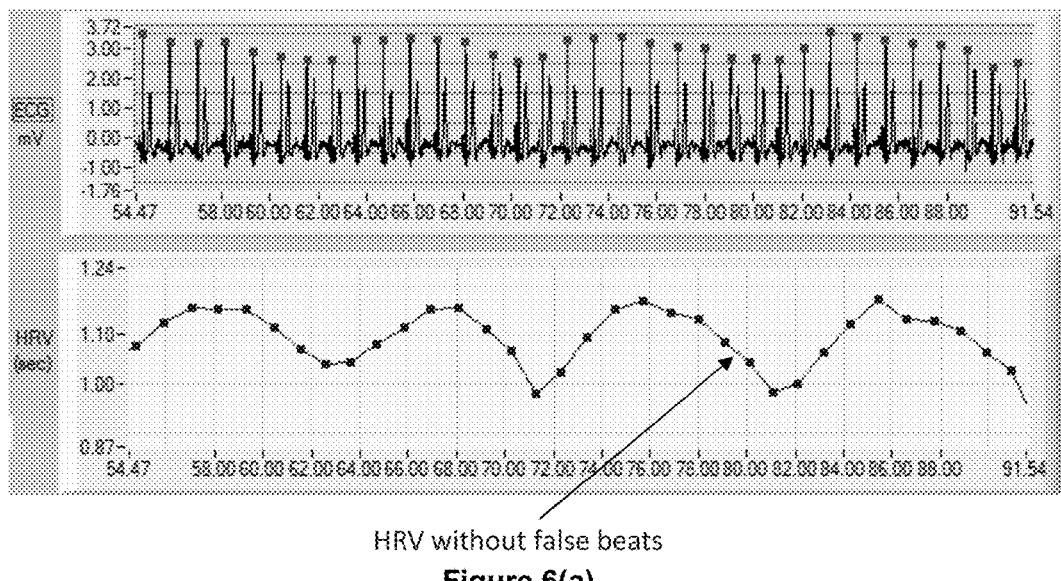
FIG. 6(*a*) shows a portion of a first ECG signal and its HRV, with the first ECG signal comprising 300 beats without adding false heartbeats.

FIG. 4 shows the parameters TAS($t_X$) and TAP($t_X$) obtained in real time by a calculation based on 30 samples of the sliding window at each moment $t_X$ (W=30). As shown in FIG. 4, the states of the sympathetic and parasympathetic systems of the person 10 are calculated in real time and shown as the sampling duration TE unfolds between the moment of departure at the $32^{th}$ second and the moment of the end at the $316^{th}$ second.

According to an advantageous but optional embodiment, the data processing module 222 furthermore carried out the calculation of the designated parameters TPSP and TPPS.

The parameter TPSP is configured to represent the rate of pollution of the sympathetic to the parasympathetic system which likely indicates a poor respiration quality of the person 10 due to the stress perceived or from a physical effort. The calculation of the parameter TPSP is calculated according to the equation (6) hereinbelow:

$$TPSP = 100 \cdot \frac{\sum_{n=1}^{N-1}(t_n - t_{n-1}) \text{ if } (a_n < a_{n-1} \text{ and } a_{n-1} > a_{n-2} \text{ and } a_{n+1} > a_n)}{\sum_{n=1}^{N-1}(t_n - t_{n-1})}$$

The parameter TPSP is calculated, using the N−1 RR intervals of the HRV derived from the ECG signal comprising N heartbeats, in such a way as to accumulate values $a_n$ if a segment between two values $a_n$ and $a_{n-1}$ is decreasing and between two adjacent rising segments of which one precedes said segment and the other follows said segment.

In other words, this rate of pollution TPSP takes a decreasing segment into account which disturbs the increasing monotonous trend, also designated as the increasing trend, formed by two rising segments of which one precedes said decreasing segment and the other follows said decreasing segment.

The sum of the values $a_n$ satisfying the conditions hereinabove is then divided by the sum of all of the values $a_1$, $a_2$ to $a_{N-1}$.

The parameter TPPS is configured to represent the rate of pollution from the parasympathetic system to the sympathetic system which likely indicates a poor respiration quality of the person 10 during rest or the recovery after a physical effort. The calculation of the parameter TPPS is represented in the equation (7) hereinbelow:

$$TPPS = 100 \cdot \frac{\sum_{n=1}^{N-1}(t_n - t_{n-1}) \text{ if } (a_n > a_{n-1} \text{ and } a_{n-1} < a_{n-2} \text{ and } a_{n+1} < a_n)}{\sum_{n=1}^{N-1}(t_n - t_{n-1})} \qquad \text{Eq. (7)}$$

The parameter TPPS is calculated, using the N−1 RR intervals of the HRV derived from the ECG signal comprising N heartbeats, in such a way as to accumulate values $a_n$ if a segment between two values $a_n$ and $a_{n-1}$ is rising and between two decreasing adjacent segments of which one precedes said segment and the other follows said segment.

In other words, this rate of pollution TPPS takes a rising segment into account which disturbed the decreasing monotonous trend, also designated as decreasing trend, formed by two decreasing segments of which one precedes said rising segment and the other follows said rising segment.

The sum of the values $a_n$ satisfying the conditions hereinabove is then divided by the sum of all of the values $a_1$, $a_2$ to $a_{N-1}$.

In another embodiment, a simplified estimation of the rates of pollutions TPSP and TPPS can be obtained by calculating the number of occurrences where the monotonous trends (increasing or decreasing) of the HRV in relation to the number of RR intervals which is N−1.

Two parameters $\overline{TPSP}$ and $\overline{TPPS}$, a simplified estimation for the parameters TPSP and TPPS respectively, are shown in the equations (8) and (9) hereinbelow:

$$\overline{TPSP} = 100 \cdot \frac{\sum_{n=1}^{N-1} 1 \text{ if } (a_n < a_{n-1} \text{ and } a_{n-1} > a_{n-2} \text{ and } a_{n+1} > a_n)}{N-1} \qquad \text{Eq. (8)}$$

-continued $$\overline{TPPS} = 100 \cdot \frac{\sum_{n=1}^{N-1} 1 \text{ if } (a_n > a_{n-1} \text{ and } a_{n-1} < a_{n-2} \text{ and } a_{n+1} < a_n)}{N-1} \qquad \text{Eq. (9)}$$

The values of the parameters $\overline{TPSP}$ and $\overline{TPPS}$ are the simplified versions of the parameters TPSP and TPPS in terms of mathematical calculations. They are considered to be approximated estimations which are in practice often close to the values of the parameters TPSP and TPPS.

As for the parameters TAS and TAP, the calculations hereinabove in order to obtain the parameters TPSP and TPPS are simple mathematical implementations, which as such makes it possible to obtain results in real time, in particular in an embodiment wherein the number N of heartbeats is less than, for example, 1000.

As such, as for the calculations of the parameters $TAS(t_X)$ and $TAP(t_X)$, the data processing module 222 carries out, at each moment such as a new heartbeat measured at the moment $t_X$ of the ECG signal, calculations of the parameters $TPSP(t_X)$ and $TPPS(t_X)$ using W heartbeats between two heartbeats (i.e. the $(X-W+1)^{th}$ and the $x^{th}$ heartbeats) respectively at moments $t_{X-W+1}$ and $t_X$ of an ECG signal.

These W heartbeats can be obtained by using a sliding window. The invention is not however limited to methods for selecting or for sampling heartbeats used for the calculations of the parameters $TPSP(t_X)$ and $TPPS(t_X)$.

In a preferred but not limiting embodiment, the calculations of the parameters $TAS(t_X)$ and $TAP(t_X)$ are carried out after the $W^{th}$ heartbeat of the ECG signal. In addition, the number of RR intervals of the HRV between the two heartbeats measured at moments $t_{X-W+1}$ and $t_X$ is W−1.

The calculation of the parameter $TPSP(t_X)$ is represented in the equation (10) hereinbelow $$TPSP(t_X) = 100 \cdot \frac{\sum_{k=X-W+2}^{X} (t_k - t_{k-1}) \text{ if } (a_k < a_{k-1} \text{ and } a_{k-1} > a_{k-2} \text{ and } a_{k+1} > a_k)}{\sum_{k=X-W+2}^{X} (t_k - t_{k-1})} \quad \text{Eq. (10)}$$

In a manner close to that of the calculation of the parameter TPSP, the parameter $TPSP(T_X)$ is calculated, using the W−1 RR intervals sampled, in such a way as to accumulate values $a_k$ if a given segment between two values $a_k$ and $a_{k-1}$ is decreasing and therefore perturbs the increasing monotonous trend formed by the two rising segments and adjacent to said given segment of which one precedes said decreasing segment and the other immediately follows said decreasing segment.

The sum of the values $a_k$ satisfying the conditions hereinabove is then divided by the sum of all of the W−1 values $a_{X-W+2}, a_{X-W+3}$ to $a_X$.

The calculation of the parameter $TPPS(t_X)$ is represented in the equation (11) hereinbelow $$TPPS(t_X) = 100 \cdot \frac{\sum_{k=X-W+2}^{X} (t_k - t_{k-1}) \text{ if } (a_k > a_{k-1} \text{ and } a_{k-1} < a_{k-2} \text{ and } a_{k+1} < a_k)}{\sum_{k=X-W+2}^{X} (t_k - t_{k-1})} \quad \text{Eq. (11)}$$

In a manner very similar to that of the calculation of the parameter TPPS, the parameter $TPPS(T_X)$ is calculated, using the W−1 RR intervals sampled, in such a way as to accumulate values $a_k$ if a given segment between two values $a_k$ and $a_{k-1}$ is rising and therefore disturbs the decreasing monotonous trend formed by the two decreasing segments and adjacent to said given segment of which one precedes said rising segment and the other follows said rising segment.

The sum of the values $a_k$ satisfying the conditions hereinabove is then divided by the sum of all of the W−1 values $a_{X-W+2}, a_{X-W+3}, \ldots, a_X$.

The parameters TPSP and TPPS represent the quality of the respiration (TPSP for inhalation and TPPS for exhalation) of the person 10. When the person 10 is in a state of rest by practicing coherent respiration, the values of the parameters TPSP and TPPS are less than 1% and can be very close to 0%. In another case wherein the person 10 is still in a state of rest but by breathing normally (without cardiac coherence), the values of the parameters TPSP and TPPS are about 10%.

The module for displaying data 130 is coupled, by a wired or wireless communication such as by radio waves, to the data processing module 222. This module for displaying data 130 is configured to receive at least one portion of the results of the method of analysis carried out by the data processing module 222 such as parameters TAS, TAP, TPSP, TPPS, $TAS(t_X)$, $TAP(t_X)$, $TPSP(t_X)$, $TPPS(t_X)$ and give a visual representation thereof on a display screen. For example, the results of the calculations of the parameters TAS and TAP as shown in FIGS. 3 and 4 are visually displayed graphically by the module for displaying data 130. Results of the calculations of the parameters TAS, TAP, TPSP, TPPS, $TAS(t_X)$, $TAP(t_X)$, $TPSP(t_X)$, $TPPS(t_X)$ can be displayed graphically or in an audible manner.

According to an embodiment, the module for displaying data 130 is incorporated into an electronic device such as a mobile telephone, a tablet, a computer, a watch, etc.

The invention is not limited to means of communication used to carry out the wired or wireless communication between the module for displaying data 130 and the data processing module 222 or to the implementation of the module for displaying data 130.

Other examples of visual representation that can be displayed on a screen are given hereinbelow:

Object (car, plane), human or animal character of which the behavior or animation varies according to the parameter or parameters calculated.

Geometric figures of which the dimensions and/or the color vary according to the parameter or parameters calculated (for example circles, ellipses, squares, triangles).

The calculations of the parameters TAS, TAP, TPSP, TPPS, $TAS(t_X)$, $TAP(t_X)$, $TPSP(t_X)$, $TPPS(t_X)$ of the method of analysis according to the invention, carried out by the data processing module 222, are temporal analyses using the HRV derived from an ECG signal.

In addition, the parameters such as hereinabove make it possible to measure and to indicate the energy level of the body of the person 10 in a state of rest or/and in activity for example during a sports activity.

The method of temporal analysis of the invention as such has several advantages hereinbelow:

1) Monitoring of the Sympathetic and Parasympathetic Systems Independently and Simultaneously:

As mentioned hereinabove, the method of the invention divides the values $a_1$, $a_2$, to $a_{N-1}$ of the RR intervals into two groups.

More precisely, the parameter TAS, reflecting the activity of the sympathetic system, is calculated in such a way as to sum only the values $a_n$ corresponding to the decreasing segments as explained hereinabove while the parameter TAP, reflecting the activity of the parasympathetic system, is calculated in such a way as to sum only the values $a_n$ that correspond to the rising segments. The two parasympathetic and sympathetic branches can as such be monitored independently in real time, which allows a person or the doctor to verify in real time the level of stress perceived (for example when the parameter TAS is greater than the parameter TAP) and to determine adapted remedies and carried out more preferably on site in order to decrease the value of the parameter TAS. The result of the remedies applied can also be verified on site and in real time. The doctor or the user can then retroact on the remedies or actions to be carried out in order to return the activity of the ANS to the desired value or return the balance between sympathetic and parasympathetic systems to the balance desired.

The parameters TPSP and TPPS use these characteristics and therefore also make it possible to show individually, during the same period of monitoring, the level of interference between the two sympathetic and parasympathetic branches of the ANS, which as such allows a person or the doctor to verify in real time the quality of the respiration.

The higher the value of the parameters TPSP and TPPS is, the lesser the quality of the respiration is. In the case of a normal and unconscious respiration, the values of the parameters TPSP and TPPS are about 10%. In the case of a coherent and symmetrical respiration, for example 5 seconds of inhalation and 5 seconds of exhalation, the values of the parameters TPSP and TPPS are substantially equal to zero.

On the other hand, the methods of frequency analysis that apply calculations such as the FFT on the HRV cannot separate the data concerning the sympathetic branch from those concerning the parasympathetic branch. In other words, the data concerning the sympathetic and parasympathetic systems are mixed and in a random manner. The separation of the data of these two systems is therefore not possible.

A person or the doctor therefore cannot determine, using the calculations obtained by the methods of frequency analysis, the activity of the sympathetic branch independently from that of the parasympathetic branch and inversely.

If a person inhales for 5 seconds and exhales for the following 5 seconds, it can be considered that the person is breathing in a coherent symmetrical manner.

FIG. 5($a$) shows a spectrum of the HRV that comprises a single spike at 0.1 Hz and corresponds to a period of respiration of 10 seconds (5 seconds of inhalation and 5 seconds of exhalation). As such, it is not possible to separate the data of the two sympathetic and parasympathetic branches using such a spectrum. Indeed, the only valid piece of information obtained from the spectrum is the respiratory frequency of which the spike is at 0.1 Hz.

In a second example, a person breathes unconsciously (random) in a state of rest. FIG. 5($b$) shows a spectrum of the HRV according to the second example.

Note that a random spectral distribution changes each time due to the change in the activity carried out by the person and/or the change in the breathing rate of the person. The spectral distribution of the HRV therefore represents the respiratory frequency comprising the data of the two branches of the ANS already cumulated and mixed in an inseparable manner in the temporal domain.

It is thus no longer possible to discriminate each component using the spectral distribution of the HRV. In other words, it is then impossible to extract the desired information using the spectral distribution of the HRV comprising the data that is inseparably mixed of the two branches of the ANS.

2) Following in Real Time:

The calculations of the temporal analysis such as hereinabove are simple mathematical implementations.

In relation to the methods of frequency analysis that involve calculations that require a complexity that is substantially greater such as the FFT, the CDM method, etc, the calculations of the parameters TAS, TAP, TPSP, TPPS, TAS($t_X$), TAP($f_X$), TPSP($t_X$), TPPS($t_X$) consume less execution time and therefore make it possible to monitor in real time the activities of the sympathetic and parasympathetic systems. It is then possible to retroact in real time in order to control the activity of the ANS.

In an embodiment of the methods of frequency analysis in real time wherein W (the number of samples of the FFT sliding window) is 20 and the heart rate is 60 beats/minute, the spectral precision is 0.05 Hz (Hertz)=1/20 Hz, and this results in that it is necessary to analyze and to separate a spectrum that spreads between 0 and 0.5 Hz with only 10 points of FFT.

As such, in order to obtain reasonable precision for example of 0.005 Hz, W should be 200, with the methods based on a frequency analysis, it is necessary to have the data from 200 heartbeats. The technique of inserting zeros (zero padding) can possibly increase the spectral resolution but does not increase the precision of the frequency analysis. An execution time of more than 3 minutes is required with a mean heart rate of for example 60 beats/minute in order to have a first result; in other words, the result of the calculations cannot easily be obtained in real time.

3) Improved Precision Thanks to the Better Signal-to-Noise Ratio and Reduced Sensitivity to False Heartbeats.

The sensitivity to false beats and/or to the various arrhythmias of the method of temporal analysis of the invention is low due to a linear dependence between the error and the result.

In an example using 300 heartbeats of which two are false beats, parameters TAS and TAP of the invention are calculated, the error rate is about 2/300=0.0066% and is therefore negligible.

Inversely, by implementing the frequency analysis and by taking the same example, two false beats lead to an effect that is much greater as shown in what follows in reference to FIGS. 6($a$) to 6($d$).

FIG. 6($a$) shows a portion of a first ECG signal and its HRV, with the first ECG signal comprising 300 beats without adding false heartbeats. FIG. 6($b$) shows a portion of a second ECG signal and its HRV, the second ECG signal being obtained by adding two false beats respectively at moments t=62 sec and t=80.5 sec to the first ECG signal.

FIGS. 6($c$) and 6($d$) respectively show the spectra of HRV obtained by carrying out a conventional frequency analysis of the HRV of the first ECG signal (without false beats) and those for the second ECG signal (with two false beats).

The spectrum shown in FIG. 6(d) is substantially affected by the noise resulting from the two false beats. The two false beats could possibly be removed manually after the end of the acquisition of an ECG signal and before the spectral analysis of the HRV, but in this case any notion of real time disappears. In addition, in a case of arrhythmia, the HRV spectra would be even more seriously affected.

As such, it is clear that the method of temporal analysis of the invention is, in relation to the methods of frequency analysis, less sensitive to noise.

4) Non-Invasive Method Able to be Used in a Sports Environment

The calculations are based on RR intervals and do not need other types of data. The RR intervals can be measured by an ECG sensor 110 in a non-invasive manner and in an environment that imposes constraints such as a sports environment.

The parameters TAS, TAP, TPSP and TPPS of the invention show effectively as such the activity of the sympathetic system and that of the parasympathetic system and thus make it possible for researchers and doctors to have a precise and reliable representation of the ANS, which as such allows them to increase the pertinence of their diagnostics and to reduce the time and therefore the cost of acquisition and obtaining the representation. A user can moreover verify his state of stress by viewing the results of said parameters, and can therefore correlate them with the emotional state of the person and/or the physical activities that the person has carried out.

These parameters can be applied to various calculations such as a calculation of the stress perceived and accumulated by a person, a calculation showing the emotional state linked to a stressful situation, or/and that of the energy expended by a player during a sports activity, etc.

One of the applications is the estimation of the stress accumulated over a long period. For example, is a person breathes in a coherent and symmetrical manner (i.e. 5 seconds of inhalation followed immediately by 5 seconds of exhalation, constituting a cardiac coherence), the result of the calculations of the parameters TAS and TAP shows that the ANS system of the person 10 is balanced. That is to say the TAS and the TAP are respectively 50% and the TAS/TAP ratio is therefore equal to 1.

However, if the person is subjected to prolonged stress, for example several weeks, months or years, the result of the calculations of the parameters TAS and TAP shows an imbalance (values of the TAS greater than that of the TAP), and reflects this state of stress.

A parameter SL configured to represent the stress level of the person 10 is represented in the equation (12):

$$SL = 100 + TAS - TAP \qquad \text{Eq. (12)}$$

This estimation of the stress level can be carried out in real time, for example, at the moment $t_X$ of the ECG signal, by using the parameters $TAS(T_X)$ and $TAP(T_X)$ such as hereinabove. The estimation of the stress level $SL(T_X)$ is represented in the equation (13):

$$SL(t_X) = 100 + TAS(t_X) - TAP(t_X) \qquad \text{Eq. (13)}$$

Figure 7A:
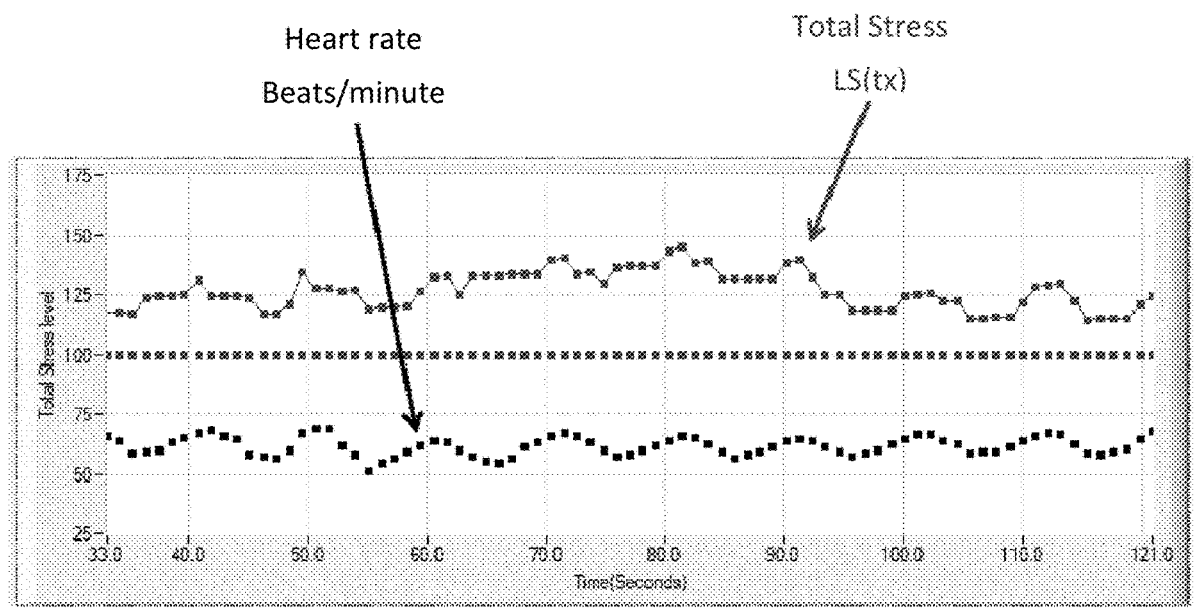
FIG. 7(*a*) shows the results of an example of a calculation of the parameter SL.

FIG. 7(a) shows the results of an example of a calculation of the parameter SL.

In this example, the person 10 has been subjected to a stress over the long term. The stress level SL is equal to 126.3%, which shows a malfunction of the ANS system with an increase in the sympathetic activity and a decrease in the parasympathetic activity. In this example, the TAP/TAS ratio is 1.68.

On the other hand, a value of the parameter SL less than 100 (i.e. the TAS/TAP ratio being less than 1) shows that the person is not undergoing any specific stress or that the impact of the stress is very limited for example due to an excellent capacity for managing stress or an environment that is not very stressful.

A value of the parameter SL equal to 100 shows that the person does not have any particular stress problems.

According to an advantageous embodiment, the data processing module 222 is configured to generate a respiration stimulus, more preferably symmetrical, intended to be supplied to the person 10 for a duration T, in such a way as to adjust the stress level of the person 10. The term symmetrical respiration designates a respiration during which the inhalation is as long as the exhalation.

The respiration stimulus comprises a visual stimulus, or/and an audible or/and olfactory stimulus. A visual stimulus comprises for example relaxing images or videos: landscape with good weather such as a sunny beach. An audible stimulus comprises for example sounds of the sea and seagulls. An olfactory stimulus comprises for example odors of the sea.

In an embodiment wherein the respiration stimulus comprises a combination of the visual, audible or/and olfactory stimuli, these visual, audible or/and olfactory stimuli are more preferably coherent with each other and generated simultaneously.

The respiration stimulus comprises a respiratory setting in such a way that the person 10 breathes symmetrically. The respiration stimulus lasts for a time T which is calculated, more preferably by the data processing module 222, according to at least the heart rate (HR). According to a preferred embodiment, the duration T is generated by using a sinusoidal signal of a frequency for example of 0.1 Hz which is obtained by sampling, with a frequency higher than 0.01 Hz, the heart rate (HR). The respiratory setting of the duration T of 10 seconds therefore comprises an inhalation of 5 seconds and an exhalation of 5 seconds. As such, the respiration stimulus is supplied to the person 10 so that the person 10 can regulate his respiration by carrying out an inhalation of 5 seconds and an exhalation of 5 seconds.

In an advantageous embodiment, the method for regulating further comprises a continuous linear correlation, carried out preferentially by the data processing module 222, according to at least the respiration stimulus and the HR by taking a number of samples of heartbeats between 10 and 30 and, more preferably 30. The calculation of the linear correlation makes it possible to estimate a level of adaptation of the ANS system of the person 10 to the setting for the respiration stimulus.

In an advantageous embodiment, the HR is calculated in real time and the duration T is calculated and adjusted also in real time by applying an equation (14) in which the HR is the heart rate of the person 10:

$$T = 10 * \left( \frac{60}{HR} \right) \qquad \text{Eq. (14)}$$

As such, the regulating of the ANS system of the person 10 is carried out in real time, thus allowing the person 10 to rapidly obtain a maximum of comfort.

In addition, a value of chronic stress CS is calculated according to the mean value of the parameter $SL(t_X)$ over said duration T of the respiration stimulus. Preferably, the value of chronic stress CS is equal to the mean value of the parameter $SL(t_X)$ over said duration T of the respiration stimulus.

Another application of these parameters relates to the estimation of the residual stress of a person during a sports activity. A parameter RSL configured to represent the residual stress level of the person 10 is represented in the equation (15):

$$RSL = SL \cdot \frac{HR_{Rest}}{HR} \quad \text{Eq. (15)}$$

This estimation of the residual stress level can be carried out in real time, for example, at the moment $t_X$ of the ECG signal. The estimation of the residual stress level $RSL(T_X)$ is represented in the equation (16):

$$RSL(t_X) = SL(t_X) \cdot \frac{HR_{Rest}}{HR(t_X)} \quad \text{Eq. (16)}$$

in which $HR_{Rest}$ is the heart rate at rest, i.e. the person 10 is inactive for at least 20 seconds and preferably 40 seconds, $HR(t_X)$ is the heart rate at the moment $t_X$.

Figure 7B:
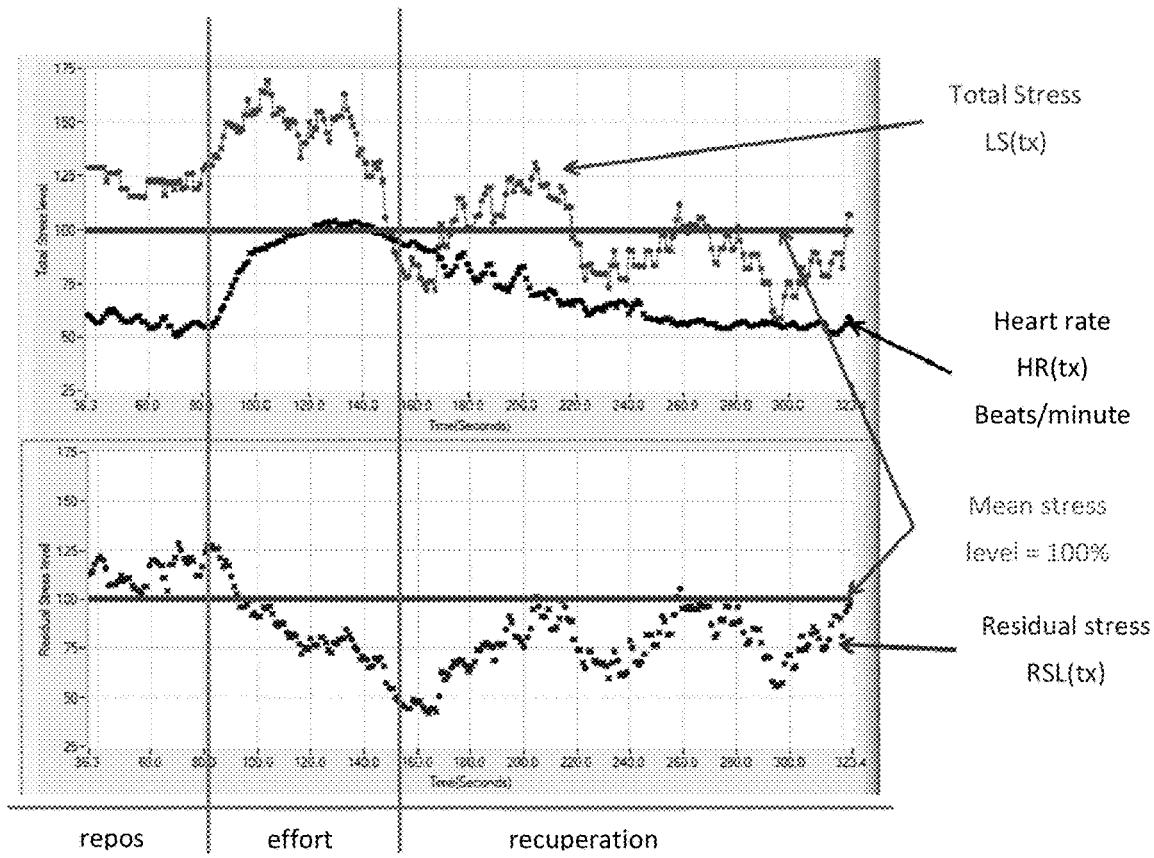

FIG. 7(b) shows the results of an example of a calculation of the parameters $SL(t_X)$, $RSL(t_X)$ and $HR(t_X)$ during a rest phase, a phase of sports activity and a recovery phase.

The parameters TAS, TAP, TPSP, TPPS, the applications such as SL, CS and RSL and declinations thereof in real time, can be used in video games and simulators in order to show the state of the ANS and therefore the emotional state of a player/patient. The stress level, the level of energy of the person can as such be detected.

As described above, the module for displaying data 130 is configured to receive at least one portion of the results of the method of analysis carried out by the data processing module 222 such as parameters TAS, TAP, TPSP, TPPS, SL, CS, RSL, $TAS(t_X)$, $TAP(t_X)$, $TPSP(t_X)$, $TPPS(t_X)$, $SL(t_X)$, $RSL(t_X)$. The module for displaying data 130 is also configured to display at least one portion of the results of the parameters hereinabove, visually (for example a graph) or/and in an audible manner.

Note that in terms of the reliability of the calculation from a mathematical standpoint, i.e. in an ideal condition wherein the ECG signal is correctly captured by the ECG sensor 110, the calculations of the parameters and of the applications proposed by the invention are, in relation to those of the known methods of frequency analysis, much more precise. The number (N or W) of beats can be reduced to a number between 20 and 40.

A possible application consists for example in taking into account the activity of one or several of these parameters relative to the ANS in order to modify the behavior of an avatar. Such can be the case in a video game or in a medical or wellness program wherein the avatar, character, animal or animated object would see their representation and/or their behavior and/or there faculties modified according to the parameters relating to the ANS.

In the framework of a video game, an objective would be to increase the realism of the game and to increase the sensation of the player.

In the framework of a medical or wellness program, an objective would be to control the ANS in order to modify the representation and/or the behavior and/or the faculties of the avatar in such a way as to achieve an objective. For example, for children, controlling the respiration would impact in real time the representation of an avatar such as an plane in flight, in such a way as to stabilize the plan on a screen, therefore encouraging the child to better control his respiration. The invention as such proposes a system for assisting with the regulating of the ANS.

As such, the visual representation in real time of the activity of the ANS of a subject makes it possible to retroact in order to modify the ANS in real time. According to the applications, this retroaction can be: controlled by the person themselves, for example in order to reduce their stress; or controlled by another person or an external system so as to provide the subject, as described above, respiration stimuli in order to modify their emotional state or their stress level.

Alternatively to a visual representation, the invention can also provide an audible or touch-sensitive representation of the parameters calculated and relating to the ANS.

The invention can also cumulate a visual, audible or touch-sensitive representation of the parameters calculated and relating to the ANS.

The invention is not limited to only the modes and embodiments described hereinabove, but extends to all of the embodiments that fall within the scope of the claims.

In particular, the invention does not extend only to the methods and systems allowing for the calculation of each one of the parameters TAS, TAP, TPSP, TPPS, SL, CS and RSL. It also extends to the methods and systems allowing for the calculation of one or of only some of the parameters TAS, TAP, TPSP, TPPS, SL, CS and RSL.

The invention claimed is:

1. A method of monitoring an autonomic nervous system (ANS) of a subject, the ANS including a sympathetic system and a parasympathetic system, the method comprising the following steps:

acquiring at least one physiological signal, with this physiological signal comprising W heartbeats, with each heartbeat being detected at a moment t, with t between $t_{X-W+1}$ and $t_X$, the moment $t_X$ being a last beat of the W heartbeats;

generating a data which is a function of a variability of a heart rate (HRV) over all of the W heartbeats, with the HRV including W−1 RR intervals separating two consecutive heartbeats detected respectively at the moments $t_{k-1}$ and $t_k$, each RR interval having a duration with a value $a_k = t_k - t_{k-1}$ with $k = (X-W+2) \ldots X$;

calculating, by using at least one microprocessor, a parameter $TAS(t_X)$ representing a level of activity of the sympathetic system and which is according to a ratio between on the one hand a first sum obtained by summing, among the values $a_k$, only those that are greater than the value $a_{k-1}$ of the immediately preceding interval and a second sum obtained by summing all of the W−1 values $a_k$;

a parameter $TAP(t_X)$ representing a level of activity of the parasympathetic system and which is according to the ratio between on the one hand a first sum obtained by summing, among the values $a_k$, only those that are less than the value $a_{k-1}$ of the immediately preceding interval and a second sum obtained by summing all of the W−1 values $a_k$; and a parameter $SL(t_X)$ representing a stress level of the subject at the moment $t_X$ by applying the following equation: $SL(t_X)=100+TAS(t_X)-TAP(t_X)$; and displaying a data representative of at least one of the parameters to supply the subject with the data representative of the at least one of the parameters.

2. The method of monitoring according to claim 1 comprising:

generating a respiration stimulus supplied to the subject for a duration T, with the respiration stimulus comprising a respiratory setting so that the subject breathes symmetrically;

the duration T being calculated according to at least one data according to a heart rate (HR) of the subject.

3. The method of monitoring according to claim 2 wherein the at least one microprocessor calculates a parameter including a value of chronic stress CS which is a function of the parameter $SL(t_X)$ during said duration T.

4. The method of monitoring according to claim 3 wherein the value of chronic stress CS is equal to the mean value of the parameter $SL(t_X)$ over said duration T of the respiration stimulus.

5. The method of monitoring according to claim 2 comprising calculating and displaying of a mathematical correlation between the heart rate (HR) of the subject and a function that controls the respiration stimulus.

6. The method of monitoring according to claim 1 wherein said at least one of the parameters includes a parameter $RSL(t_X)$ relative to the residual stress level of the subject at the moment $t_X$ and calculated by applying the following equation:

$$RSL(t_X) = SL(t_X) \cdot \frac{HR_{Rest}}{HR(t_X)}$$

in which $HR_{Rest}$ is the heart rate at rest, i.e. the subject is inactive for a duration of rest comprised of at least 20 seconds, $HR(t_X)$ is the heart rate at the moment $t_X$.

7. The method of monitoring according to claim 1 comprising calculating at least one of the following two parameters:

a parameter $TPSP(t_X)$ representing a rate of pollution from the sympathetic system to the parasympathetic system and which is according to a ratio between on the one hand a first sum obtained by summing, among the values $a_k$, only those that satisfy the following condition: $a_k<a_{k-1}$ and $a_{k-1}>a_{k-2}$ and $a_{k+1}>a_k$ and on the other hand a second sum obtained by summing all of the W-1 values $a_k$; or a parameter $TPPS(t_X)$ representing a rate of pollution from the parasympathetic system to the sympathetic system and which is according to a ratio between on the one hand a first sum obtained by summing, among the values $a_k$, only those that satisfy the following condition: $a_k>a_{k-1}$ and $a_{k-1}<a_{k-2}$ and $a_{k+1}<a_k$ and on the other hand a second sum obtained by summing all of the W-1 values $a_k$.

8. The method of monitoring according to claim 7 wherein said at least one of the parameters is the $TAS(t_X)$ representing the level of activity of the sympathetic system and wherein the $TAS(t_X)$ is calculated by applying the following equation:

$$TAS(t_X) = 100 \cdot \frac{\sum_{k=X-W+2}^{X} (t_k - t_{k-1}) \text{ if } (a_k \leq a_{k-1})}{\sum_{k=X-W+2}^{X} (t_k - t_{k-1})}$$

in which:

$a_{k-1}$=value of the interval of time immediately preceding the internal of time of duration $a_k$, i.e. $a_{k-1}=t_{k-1}-t_{k-2}$, k=(X-W+2), (X-W+3) ... X.

9. The method of monitoring according to claim 7 wherein said at least one of the parameters is the $TPSP(t_X)$ and wherein the $TPSP(t_X)$ is calculated by applying the following equation:

$$TPSP(t_X) = 100 \cdot \frac{\sum_{k=X-W+2}^{X} (t_k - t_{k-1}) \text{ if } (a_k < a_{k-1} \text{ and } a_{k-1} > a_{k-2} \text{ and } a_{k+1} > a_k)}{\sum_{k=X-W+2}^{X} (t_k - t_{k-1})}$$

in which:

$a_{k-1}$=value of the interval of time immediately preceding the internal of time of duration $a_k$, i.e. $a_{k-1}=t_{k-1}-t_{k-2}$, k=(X-W+2), (X-W+3) ... X.

10. The method of monitoring according to claim 1 wherein said at least one of the parameters is the $TAP(t_X)$ representing the level of activity of the parasympathetic system and wherein the $TAP(t_X)$ is calculated by applying the following equation:

$$TAP(t_X) = 100 \cdot \frac{\sum_{k=X-W+2}^{X} (t_k - t_{k-1}) \text{ if } (a_k \geq a_{k-1})}{\sum_{k=X-W+2}^{X} (t_k - t_{k-1})}$$

in which:

$a_{k-1}$=value of the interval of time immediately preceding the internal of time of duration $a_k$, i.e. $a_{k-1}=t_{k-1}-t_{k-2}$, k=(X-W+2), (X-W+3) ... X.

11. The method of monitoring according to claim 7 wherein said at least one of the parameters is the $TPPS(t_X)$ and wherein the $TPPS(t_X)$ is calculated by applying the following equation:

$$TPPS(t_X) = 100 \cdot \frac{\sum_{k=X-W+2}^{X} (t_k - t_{k-1}) \text{ if } (a_k > a_{k-1} \text{ and } a_{k-1} < a_{k-2} \text{ and } a_{k+1} < a_k)}{\sum_{k=X-W+2}^{X} (t_k - t_{k-1})}$$

in which:

$a_{k-1}$=value of the interval of time immediately preceding the internal of time of duration $a_k$, i.e. $a_{k-1}=t_{k-1}-t_{k-2}$, k=(X-W+2), (X-W+3) ... X.

12. The method of monitoring according to claim 1 wherein a parameter TPSP is calculated representing an approximate rate of pollution of the sympathetic system to the parasympathetic system and calculated by applying the following equation:

$$\overline{TPSP} = 100 \cdot \frac{\sum_{n=1}^{N-1} 1 \text{ if } (a_n < a_{n-1} \text{ and } a_{n-1} > a_{n-2} \text{ and } a_{n+1} > a_n)}{N-1}.$$

13. The method of monitoring according to claim 1 wherein a parameter TPPS is calculated representing an approximate rate of pollution from the parasympathetic system to the sympathetic system and calculated by applying the following equation:

$$\overline{TPPS} = 100 \cdot \frac{\sum_{n=1}^{N-1} 1 \text{ if } (a_n > a_{n-1} \text{ and } a_{n-1} < a_{n-2} \text{ and } a_{n+1} < a_n)}{N-1}.$$

14. The method of monitoring according to claim 1 wherein said displaying the data representative of said at least one of the parameters comprises at least one of:
   supplying of a visual representation of said at least one of the parameters;
   supplying of an audible representation of said at least one of the parameters;
   supplying of a visual and audible representation of said at least one of the parameters; or
   displaying on a screen of one from among the following devices: a watch, a telephone, a portable computer, a tablet.

15. The method of monitoring according to claim 1 wherein said at least one of the parameters is calculated in real time or at regular intervals and said displaying the data representative of said at least one of the parameters includes supplying a visual representation of the change over time of said at least one of the parameters.

16. The method of monitoring according to claim 1 wherein at least two parameters are calculated, with at least one of the parameters being taken from the TAS($t_X$) and the TPSP($t_X$) and at least one other parameter taken from the TAP($t_X$) and the TPPS($t_X$) and said displaying the data representative of said at least one of the parameters includes supplying a visual representation of said at least two parameters, said at least two parameters being represented independently from one another.

17. The method of monitoring according to claim 1 wherein said at least one of the parameters is calculated in real time and wherein a visual representation of the change over time of said at least one of the parameters comprises displaying at least any one of:
   at least an avatar of which the animation or the visual change is a function of the change over time of said at least one of the parameters;
   at least one animated object of which the animation or the visual change is a function of the change over time of said at least one of the parameters;
   a graph that changes over time; or
   a bar that changes over time.

18. The method of monitoring according to claim 17 wherein the physiological signal is an electrocardiogram signal (ECG).

19. A computer program product comprising instructions stored on a non-transitory computer readable medium, which when they are carried out by at least one processor, execute the method as claimed in claim 17.

20. The method of monitoring according to claim 1 wherein said at least one of the parameters includes a parameter RSL($t_X$) relative to the residual stress level of the subject at the moment $t_X$, and calculated by applying the following equation:

$$RSL(t_X) = SL(t_X) \cdot \frac{HR_{Rest}}{HR(t_X)}$$

in which $HR_{Rest}$ is the heart rate at rest, i.e. the subject is inactive for a duration of rest comprised of 40 seconds, HR($t_X$) is the heart rate at the moment $t_X$.

21. A system for monitoring the autonomic nervous system (ANS) of a subject, comprising
   a sensor configured to receive the data from a physiological signal comprising W heartbeats, with each heartbeat being detected at a moment t, with t between $t_{X-W+1}$ and $t_X$, the moment $t_X$, being the last beat of the W heartbeats;
   at least one data processing module provided with at least one processor configured to execute the following steps:
   generating of a data which is a function of the variability of the heart rate (HRV) over all of the W heartbeats, with the HRV comprising W−1 RR intervals separating two consecutive heartbeats detected respectively at the moments $t_{k-1}$ and $t_k$, each RR interval having a duration with a value $a_k = t_k - t_{k-1}$ with k=(X−W+2) . . . X;
   calculating:
      a parameter TAS ($t_X$) representing the level of activity of the sympathetic system and which is according to the ratio between on the one hand a first sum obtained by summing, among the values $a_k$, only those that are greater than the value $a_{k-1}$ of the immediately preceding interval and a second sum obtained by summing all of the W−1 values $a_k$;
      a parameter TAP(tX) representing the level of activity of the parasympathetic system and which is according to the ratio between on the one hand a first sum obtained by summing, among the values $a_k$, only those that are less than the value $a_{k-1}$ of the immediately preceding interval and a second sum obtained by summing all of the W−1 values $a_k$; and
      a parameter SL($t_X$) representing a stress level of the subject at the moment $t_X$ and calculated by applying the following equation:

$SL(t_X) = 100 + TAS(t_X) - TAP(t_X)$; and a device for displaying, coupled to the data processing module and configured to supply the subject with a data representative of at least one of the parameters.

* * * * *